United States Patent
Ziegler et al.

(10) Patent No.: US 10,376,697 B2
(45) Date of Patent: Aug. 13, 2019

(54) MONTAGE DESIGN FOR CLOSED LOOP SENSING AND NEUROSTIMULATION OF THE DORSAL LATERAL PREFRONTAL CORTEX AND/OR MOTOR CORTEX

(71) Applicant: HRL Laboratories, LLC, Malibu, CA (US)

(72) Inventors: Matthias Ziegler, Oakton, VA (US); Jaehoon Choe, Agoura Hills, CA (US); Matthew E. Phillips, Calabasas, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/148,793

(22) Filed: May 6, 2016

(65) Prior Publication Data
US 2017/0312518 A1    Nov. 2, 2017

Related U.S. Application Data

(63) Continuation-in-part of application No. 15/066,813, filed on Mar. 10, 2016.
(Continued)

(51) Int. Cl.
*A61N 1/36* (2006.01)
*A61N 1/04* (2006.01)
(Continued)

(52) U.S. Cl.
CPC ........ *A61N 1/36025* (2013.01); *A61B 5/0075* (2013.01); *A61B 5/0478* (2013.01);
(Continued)

(58) Field of Classification Search
CPC ...... A61N 1/04; A61N 1/0404; A61N 1/0408; A61N 1/0456; A61N 1/0472;
(Continued)

(56) References Cited

U.S. PATENT DOCUMENTS

| | | |
|---|---|---|
| 6,457,975 B1 | 10/2002 | Miranda |
| 8,798,707 B2 | 8/2014 | Choi et al. |

(Continued)

FOREIGN PATENT DOCUMENTS

| | | |
|---|---|---|
| WO | 2005-092183 | 10/2005 |
| WO | 2013-192582 | 12/2013 |
| WO | 2016/182947 A1 | 11/2016 |

OTHER PUBLICATIONS

Dutta et al. jDevelopment of an EEG-fNIRS based online monitoring tool towards delivery of non-invasive brain stimulation. Conference: 36th Annual International Conference of the IEEE Engineering in Medicine and Biology Society (EMBC'14), At Chicago. Aug. 2014.*

(Continued)

*Primary Examiner* — Eugene T Wu
(74) *Attorney, Agent, or Firm* — Tope-McKay & Associates

(57) ABSTRACT

Described is a system for automatic adjustment of neurostimulation. The system controls stimulation of specific neural regions through a neural device positioned on a human subject, while simultaneously performing recordings from the neural device using a targeted arrangement of stimulating electrodes and distinct types of recording electrodes and sensors of the neural device. Stimulation of the specific neural regions is adjusted in real-time based on the recordings from the neural device.

12 Claims, 8 Drawing Sheets

Related U.S. Application Data

(60) Provisional application No. 62/131,031, filed on Mar. 10, 2015, provisional application No. 62/159,151, filed on May 8, 2015.

(51) Int. Cl.
  *A61N 1/20* (2006.01)
  *A61B 5/0478* (2006.01)
  *A61B 5/00* (2006.01)

(52) U.S. Cl.
  CPC .......... *A61B 5/4836* (2013.01); *A61N 1/0456* (2013.01); *A61N 1/0484* (2013.01); *A61N 1/20* (2013.01); *A61N 1/205* (2013.01)

(58) Field of Classification Search
  CPC ...... A61N 1/0476; A61N 1/0484; A61N 1/20; A61N 1/205; A61N 1/36014; A61N 1/36025; A61N 2001/36039; A61N 2001/36092; A61B 5/0476; A61B 5/0478; A61B 5/0482; A61B 5/0484; A61B 5/0075; A61B 5/18; A61B 5/4064; A61B 5/4836; A61B 5/6803; A61B 5/6814; A61B 2503/22; A61B 2505/09; A61B 2562/06; A61B 2562/066; A61B 2576/026
  See application file for complete search history.

(56) References Cited

U.S. PATENT DOCUMENTS

| | | | |
|---|---|---|---|
| 8,831,733 | B2 | 9/2014 | Wilke et al. |
| 9,149,599 | B2 | 10/2015 | Walter |
| 2005/0203366 | A1 | 9/2005 | Donoghue |
| 2006/0217781 | A1* | 9/2006 | John ................. A61N 1/36017 607/45 |
| 2010/0003656 | A1 | 1/2010 | Kilgard |
| 2010/0268287 | A1 | 10/2010 | Celnik |
| 2011/0159467 | A1 | 6/2011 | Peot |
| 2011/0224528 | A1 | 9/2011 | Choi |
| 2011/0263968 | A1 | 10/2011 | Quattrocki-Knight |
| 2012/0184870 | A1 | 7/2012 | Shaw |
| 2013/0046206 | A1 | 2/2013 | Preminger |
| 2013/0225953 | A1* | 8/2013 | Oliviero ............... A61N 1/0408 600/323 |
| 2013/0338738 | A1 | 12/2013 | Garcia Molina |
| 2014/0018882 | A1 | 1/2014 | Wilke |
| 2014/0038147 | A1 | 2/2014 | Morrow |
| 2014/0288614 | A1 | 9/2014 | Hagedorn |
| 2015/0005568 | A1 | 1/2015 | Chib |
| 2015/0005840 | A1 | 1/2015 | Pal |
| 2015/0050623 | A1 | 1/2015 | Falash |
| 2015/0079560 | A1 | 3/2015 | Cowan |
| 2015/0105837 | A1* | 4/2015 | Aguilar Domingo ...................... A61N 1/36025 607/45 |
| 2015/0140528 | A1 | 5/2015 | Sikstrom |
| 2015/0141529 | A1 | 5/2015 | Hargrove |
| 2015/0174418 | A1* | 6/2015 | Tyler ...................... A61B 5/055 601/2 |
| 2015/0187227 | A1 | 7/2015 | Zhang |
| 2015/0190635 | A1 | 7/2015 | Neuvonen |
| 2015/0297108 | A1 | 10/2015 | Chase |
| 2016/0206871 | A1* | 7/2016 | Weisend ............... A61N 1/0476 |

OTHER PUBLICATIONS

Bullard et al. Transcranial direct current stimulation's effect on novice versus experienced learning. Experimental Brain Research, vol. 213, Issue 1, pp. 9-14. Aug. 2011.*

Dutta, Anirban. Electroencephalography (EEG)-near-infrared spectroscopy (NIRS) based online imaging during non-invasive electrical brain stimulation. Master's Thesis. Sep. 2014.*

McKendrick et al. Wearable functional near infrared spectroscopy (fNIRS) and transcranial direct current stimulation (tDCS): expanding vistas for neurocognitive augmentation. Front Syst Neurosci. 2015; 9: 27. Published online Mar. 9, 2015. doi: 10.3389/fnsys.2015.00027.*

Dmochowski et al. "Optimized multi-electrode stimulation increases focality and intensity at target". Journal of Neural Engineering, vol. 8, No. 4. Jun. 10, 2011.*

Clark et al. "TDCS guided using fMRI significantly accelerates learning to identify concealed objects". NeuroImage, vol. 59, Issue 1, Jan. 2, 2012, pp. 117-128.*

Phillips et al. "A Neurostimulation-based Advanced Training System for Human Performance Augmentation". Brain Stimulation, vol. 7, Issue 2, Mar.-Apr. 2014, pp. e11-e12.*

Coffman et al. "Battery powered thought: Enhancement of attention, learning, and memory in healthy adults using transcranial direct current stimulation". NeuroImage, vol. 85, Part 3, Jan. 15, 2014, pp. 895-908.*

Choe J, Coffman BA Bergstedt DT, Ziegler MD, Phillips ME. Transcranial Direct Current Stimulation Modulates Neuronal Activity and Learning in Pilot Training. Frontiers in Human Neuroscience. 2016;10:34. doi:10.3389/fnhum.2016.00034.*

Datta et al. in "Validation of finite element model of transcranial electrical stimulation using scalp potentials: Implications for clinical dose," J Neural Engineering 2013;10(3), pp. 036018-1-036018-10.

Notification of Transmittal of International Search Report and the Written Opinion of the International Searching Authority for PCT/US2016/031321; dated Aug. 16, 2016.

International Search Report of the International Searching Authority for PCT/US2016/031321; dated Aug. 16, 2016.

The Written Opinion of the International Searching Authority for PCT/US2016/031321; dated Aug. 16, 2016.

Alloway, T.P., and Alloway, R.G. "Investigating the predictive roles of working memory and IQ in academic attainment." Journal of experimental child psychology 106.1 (2010): pp. 20-29.

Ayaz, H., Bunce, S., Shewokis, P., Izzetoglu, K., Willems, B., and Onaral, B. "Using brain activity to predict task performance and operator efficiency." Advances in Brain Inspired Cognitive Systems. (2012): pp. 147-155.

Ehrman, M. "A Study of the Modem Language Aptitude Test for Predicting Learning Success and Advising Students." Language Aptitude Invitational Symposium Program Proceedings. Arlington, VA, Sep. 25-27, 1994, pp. 74-99.

Ford, J. Kevin, and Douglas Sego. "Linking training evaluation to training needs assessment: A conceptual model." Michigan State Univ East Lansing Dept Of Psychology, 1990, pp. 1-27.

Gott, Sherrie P. "Rediscovering learning: acquiring expertise in real world problem solving tasks." No. AL/HR-TP-1997-0009. Armstrong Lab Brooks AFB, TX Human Resources Directorate, 1998, pp. 1-33.

Harrison, J., Izzetoglu, K., Ayaz, H., Willems, B., Hah, S., Ahlstrom, U., and Onaral, B. "Cognitive Workload and Learning Assessment During the Implementation of a Next-Generation Air Traffic Control Technology Using Functional Near-Infrared Spectroscopy." (2014), pp. 429-440.

Hunter, D.R. "Measuring general aviation pilot judgment using a situational judgment technique." The International Journal of Aviation Psychology 13, No. 4 (2003): pp. 373-386.

Hunter, D.R. "Airman Research Questionnaire. Methodology and Overall Results." No. DOT/FAA/AM-95/27. Federal Aviation Administration Washington Dc Office Of Aviation Medicine, 1995, pp. 1-A16.

Redick, T.S., et al. "No evidence of intelligence improvement after working memory training: a randomized, placebo-controlled study." Journal of Experimental Psychology: General 142.2 (2013): pp. 359-379.

Sohn, Y.W., and Doane, S.M. 2004. "Memory Processes of Flight Situation Awareness: Interactive Roles of Working Memory Capacity, Long-Term Working Memory, and Expertise." Human Factors: Journal of the Human Factors and Ergonomics Society 46 (3): pp. 461-475.

(56) References Cited

OTHER PUBLICATIONS

Notification of Transmittal of International Search Report and the Written Opinion of the International Searching Authority for PCT/US2016/021841; dated Oct. 12, 2016.
International Search Report of the International Searching Authority for PCT/US2016/021841; dated Oct. 12, 2016.
The Written Opinion of the International Searching Authority for PCT/US2016/021841; dated Oct. 12, 2016.
Hesse, S. et al., Combined transcranial direct current stimulation and robot-assisted arm training in subacute stroke patients: a pilot study. Restorative Neurology and Neuroscience, 2007, vol. 25, pp. 9-15.
Snowball, A. et al., Long-term enhancement of brain function and cognition using cognitive training and brain stimulation. Current Biology, 2013, vol. 23, No. 11, pp. 987-992.
Beeli, G. et al., Brain stimulation modulates driving behavior. Behavioral and Brain Functions, 2008, vol. 4, Article No. 34, internal pp. 1-7.
Choe, J. et al. Transcranial direct current stimulation modulates neuronal activity and learning in pilot training. Frontiers in Human Neuroscience, Feb. 2016, vol. 10, Article No. 34, internal pp. 1-25.
Office Action 1 for U.S. Appl. No. 15/066,813, dated May 23, 2017.
M. Scheldrup, "Transcranial direct current stimulation facilitates cognitive multi-task performance differently depending on anode location and subtasl," Frontiers in Human Neuroscience, Sep. 18, 2014, pp. 1-13.
Response to Office Action 1 for U.S. Appl. No. 15/066,813, dated Sep. 25, 2017.
Office Action 2 for U.S. Appl. No. 15/066,813, dated Oct. 26, 2017.
Response to Office Action 2 for U.S. Appl. No. 15/066,813, dated Jan. 25, 2018.
Notification Concerning Transmittal of International Preliminary Report on Patentability for PCT/US2016/021841; dated Sep. 21, 2017.
International Preliminary Report on Patentability for PCT/US2016/021841; dated Sep. 21, 2017.
Notification Concerning Transmittal of International Preliminary Report on Patentability for PCT/US2016/031321; dated Nov. 23, 2017.
International Preliminary Report on Patentability for PCT/US2016/031321; dated Nov. 23, 2017.
Office Action 3 for U.S. Appl. No. 15/066,813, dated Mar. 15, 2018.
Response to Office Action 3 for U.S. Appl. No. 15/066,813, dated Jul. 12, 2018.
Communication pursuant to Rules 161(2) and 162 EPC for European Regional Phase Patent Application No. 16762544.1, dated Oct. 17, 2017.
Response to the communication pursuant to Rules 161(2) and 162 EPC for European Regional Phase Patent Application No. 16762544.1, dated Apr. 26, 2018.
Communication pursuant to Rules 70(2) and 70a(2) EPC for the application for European Regional Phase Patent Application No. 16762544.1, dated Oct. 8, 2018.
Communication pursuant to Rules 161(2) and 162 EPC for European Regional Phase Patent Application No. 16793277.1, dated Dec. 20, 2017.
Response to the communication pursuant to Rules 161(2) and 162 EPC for European Regional Phase Patent Application No. 16793277.1, dated Jun. 22, 2018.
Office Action 4 for U.S. Appl. No. 15/066,813, dated Sep. 14, 2018.
Response to Office Action 4 for U.S. Appl. No. 15/066,813, dated Jan. 14, 2019.
A Multimodal fNIRS and EEG-Based BCI Study on Motor Imagery and Passive Movement; Yu; Sep. 8, 2013; http://www.ntu.edu.sg/home/ctguan/Publications/C_2013_Juanhong_IEEE_EMBS-NER.pdf.

\* cited by examiner

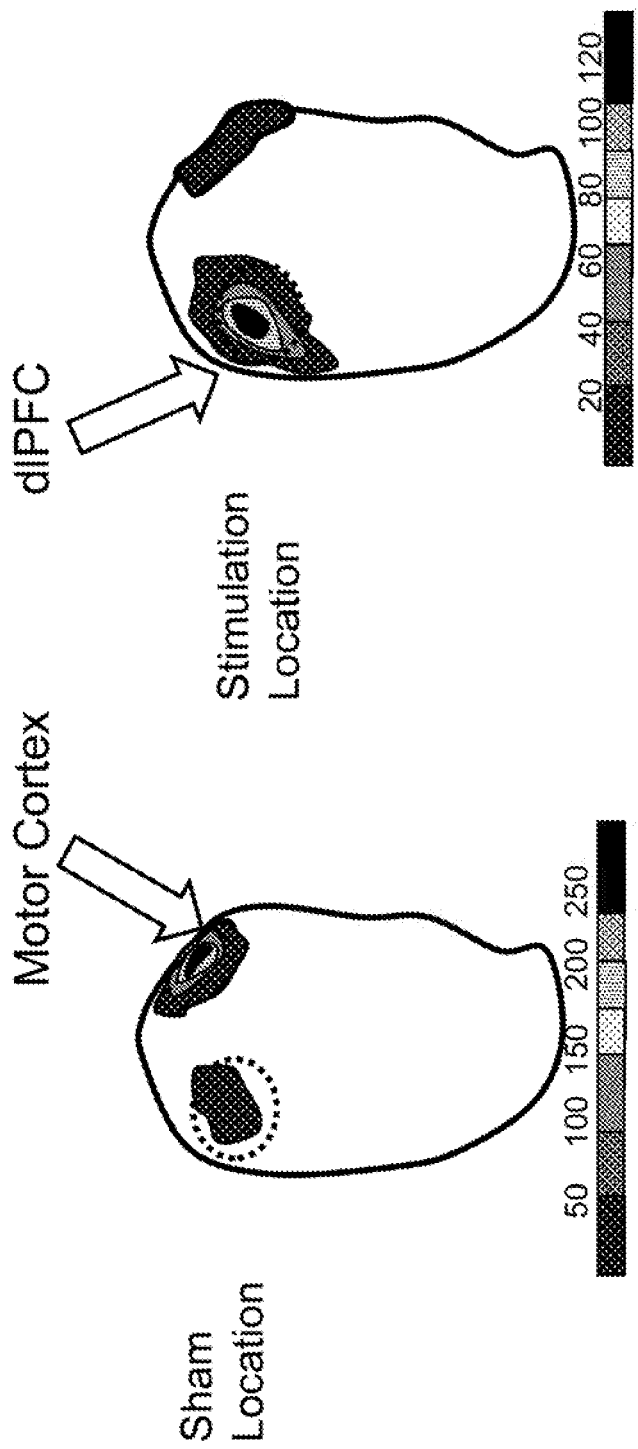

MONTAGE DESIGN FOR CLOSED LOOP SENSING AND NEUROSTIMULATION OF THE DORSAL LATERAL PREFRONTAL CORTEX AND/OR MOTOR CORTEX

CROSS-REFERENCE TO RELATED APPLICATIONS

This is a Continuation-in-Part Application of U.S. application Ser. No. 15/066,813, filed in the United States on Mar. 10, 2016, entitled, "System and Method for Training and Assessment," which is a Non-Provisional Application of U.S. Provisional Application No. 62/131,031, filed in the United States on Mar. 10, 2015, entitled, "A Method for Pilot Training and Assessment," the entirety of which are incorporated herein by reference.

This is also a Non-Provisional Application of U.S. Provisional Patent Application No. 62/159,151 filed May 8, 2015, entitled, "Montage Design for Closed Loop Sensing and Neurostimulation of the Dorsal Lateral Prefrontal Cortex and/or Motor Cortex," the entirety of which is incorporated herein by reference.

BACKGROUND OF INVENTION

(1) Field of Invention

The present invention relates to a system for adjusting neurostimulation and, more particularly, to a system for adjusting neurostimulation based on real-time sensing of brain states.

(2) Description of Related Art

Neurostimulation is a therapeutic activation of part of the nervous system using electrodes. Current techniques use a combination of electroencephalogram (EEG)/transcranial direct-current stimulation (tDCS) or functional near-infrared spectroscopy (fNIRS)/tDCS to target a variety of regions. Current state-of-the-art montages only provide either high temporal resolution (EEG) or high spatial resolution (fNIRS) information and do not provide all possible information about the current state of the brain, leading to possible misalignment and settings for neurostimulation.

Currently, brain imaging and planning of new stimulation occurs after the stimulation has been completed, such as described by Datta et al. in "Validation of finite element model of transcranial electrical stimulation using scalp potentials: Implications for clinical dose," *J Neural Engineering* 2013; 10(3), which is hereby incorporated by reference as though fully set forth herein. While operable for imaging after stimulation, such existing methods do not allow for simultaneous stimulation and recording or imaging. Thus, a continuing need exists for a system for adapting neurostimulation based on simultaneous recordings of the brain.

SUMMARY OF THE INVENTION

The present invention relates to a system for adjusting neurostimulation and, more particularly, to a system for adjusting neurostimulation based on real-time sensing of brain states. The system comprises one or more processors and a memory having instructions such that when the instructions are executed, the one or more processors perform multiple operations. The system stimulates specific neural regions through a neural device, while simultaneously performing recordings from the neural device using a targeted arrangement of stimulating electrodes and distinct types of recording electrodes and sensors of the neural device. Stimulation of the specific neural regions is adjusted in real-time based on the recordings from the neural device.

In another aspect, the system sets stimulation parameters to optimize any neural changes recorded by the recording electrodes and sensors to match a desired neural activity.

In another aspect, the system provides feedback of both temporal neural changes and region specific neural changes via electroencephalogram (EEG) electrodes and functional near-infrared spectroscopy (fNIRS) sensors.

In another aspect, preferred positions of stimulating electrodes on the neural device are provided that will focus effects of the stimulation on the specific neural regions while still allowing concentrated recordings of the specific neural regions.

In another aspect, stimulation is applied to a specific brain region, wherein the stimulation to be applied is determined by stimulation parameters determined based on prior recordings.

In another aspect, the stimulation is adjusted to decrease stimulation in one brain region and increase stimulation in another brain region.

In another aspect, the present invention comprises a method for automatic adjustment of neurostimulation. A targeted arrangement of stimulating electrodes and distinct types of recording electrodes and sensors is created for individualized stimulation. Stimulation of specific neural regions through a neural device, while simultaneously performing recordings from the neural device using the targeted arrangement of stimulating electrodes and distinct types of recording electrodes and sensors. Stimulation of the specific neural regions is adjusted in real-time based on the recordings from the neural device.

In another aspect, the neural device is a neural cap.

In another aspect, the present invention also comprises a method for causing a processor to perform the operations described herein.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 4A is an illustration of a control condition according to embodiments of the present disclosure;

FIG. 4B is an illustration of a stimulation condition according to embodiments of the present disclosure;

DETAILED DESCRIPTION

Figure 1:
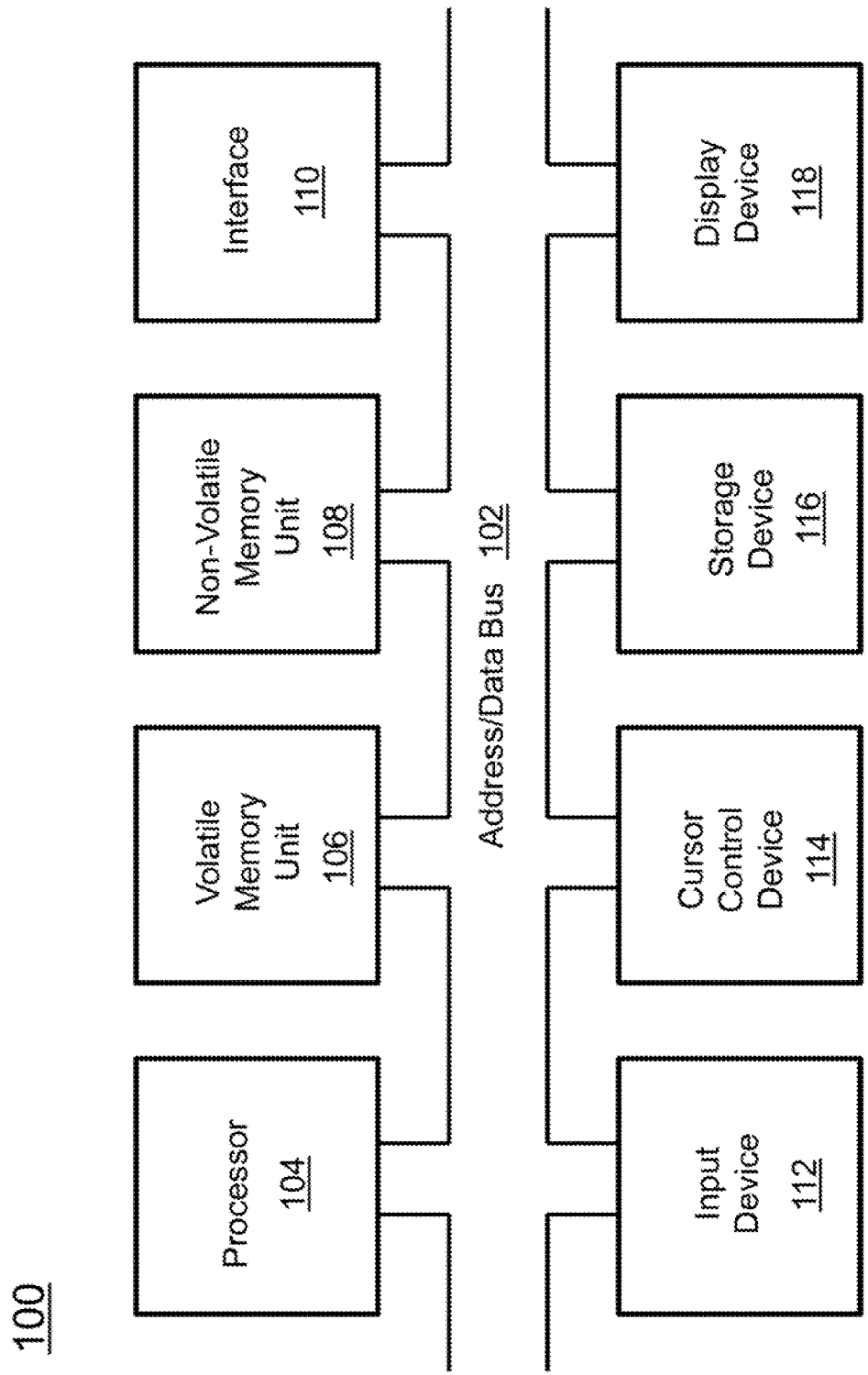
FIG. 1 is a block diagram depicting the components of a system for adjusting neurostimulation according to embodiments of the present disclosure.

The present invention relates to a system for adjusting neurostimulation and, more particularly, to a system for adjusting neurostimulation based on real-time sensing of brain states. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

(1) Principal Aspects

Various embodiments of the invention include three "principal" aspects. The first is a system for adjusting neurostimulation. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
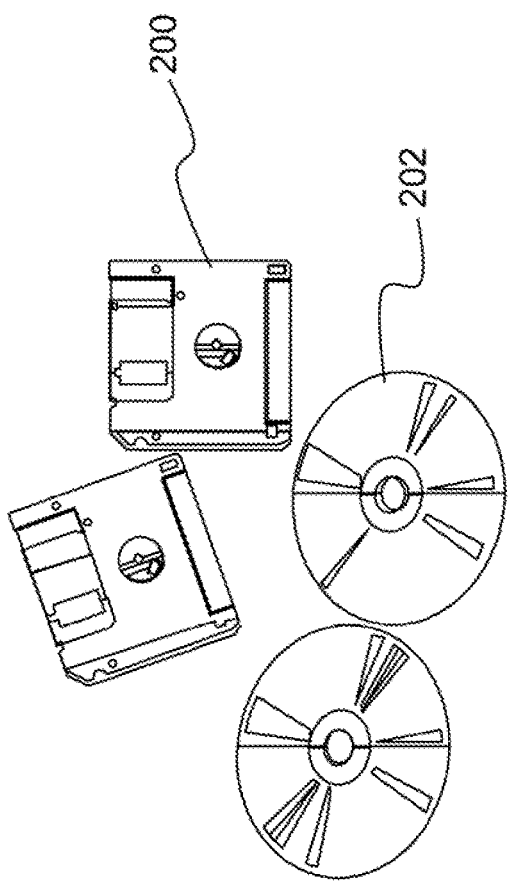
FIG. 2 is an illustration of a computer program product according to embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(2) Specific Details of Various Embodiments

Described is a method for using non-invasive transcranial direct current stimulation (tDCS) of neurons in specific regions of the brain (e.g., motor cortex and/or dorsal lateral prefrontal cortex (dlPFC)) while simultaneously recording neural activity via electroencephalography (EEG) from the entire brain and functional near-infrared spectroscopy (fNIRS) from specific regions of the brain (e.g., motor cortex and dlPFC).

In the invention described herein, the specific placement of each electrode and sensor for stimulating and recording allows for a novel focality in stimulation to the desired regions (based on an average adult male's head) while also allowing for full coverage from the recording electrodes and sensors. The ability to monitor the brain activity of, for instance, the dlPFC and motor cortex in real-time allows for a closed-loop system that will alter the stimulation settings to match desired dlPFC and motor cortex neural activity.

The system according to embodiments of the present disclosure provides a unique approach to stimulating and recording from specific brain regions such that the different modalities cause minimal interference with each other while maintaining full coverage of the regions of interest. While each of the modalities (e.g., EEG, fNIRS, tDCS) has been used individually to target the motor cortex and dlPFC, the system according to various embodiments of the present disclosure uses all three modalities simultaneously.

By using this "montage" of electrodes and sensors, there is an unprecedented level of coverage to monitor the effects of neural stimulation to the motor cortex and/or the dlPFC in real-time. This will improve the ability to accurately set the levels of stimulation to optimize any neural changes to match the desired activity. By using EEG and fNIRS, the present invention will provide feedback of both temporal brain changes (via EEG) and region specific changes (via fNIRS).

The ability to monitor brain states in real-time during stimulation will allow adjustments to be made to the stimulation setting based off of the changes to the activation pattern caused by the neurostimulation. Currently, brain imaging and planning of new stimulation occurs after the stimulation has been completed. By having localized brain imaging of the regions being stimulated, the system described herein has the unique ability to monitor and adapt stimulation settings to reach a desired change in neural activity.

Figure 3:
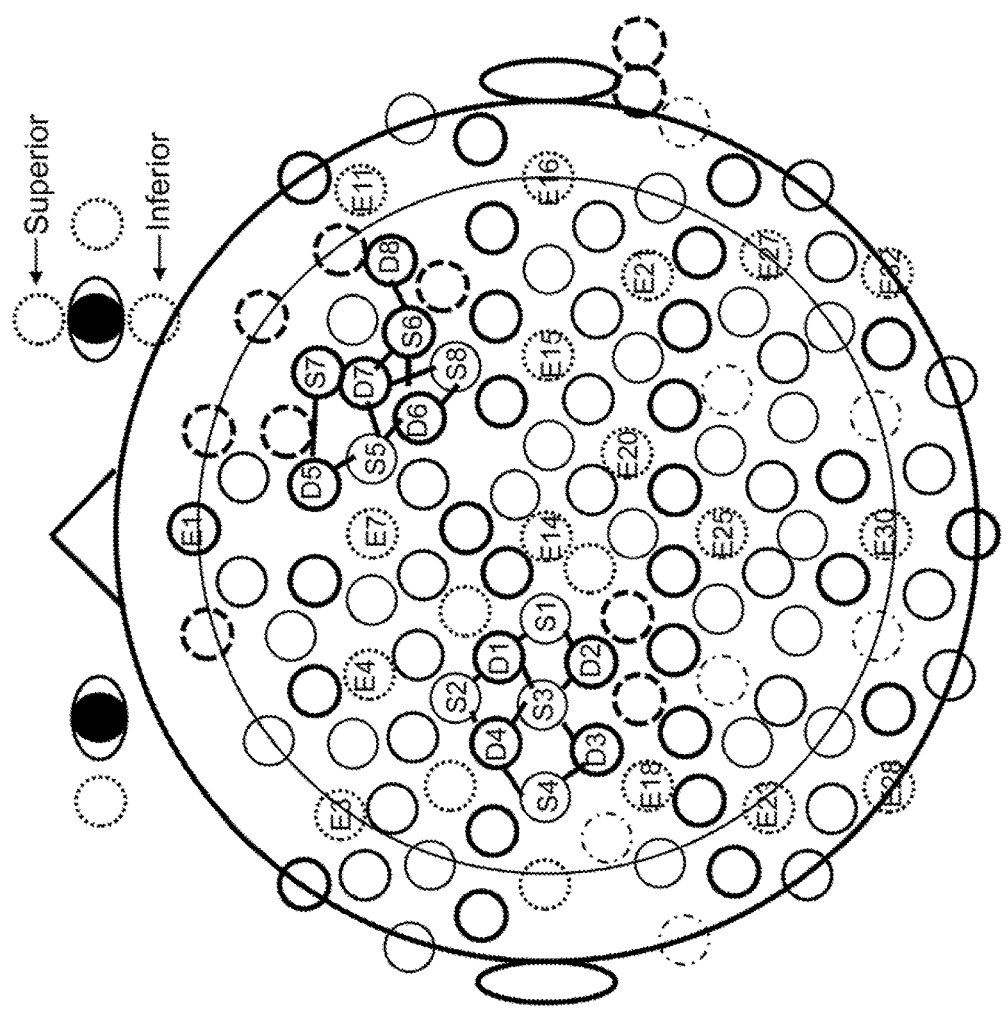
FIG. 3 is an illustration of an example arrangement of functional near-infrared spectroscopy (fNIRS), electroencephalography (EEG), and transcranial direct-current stimulation (tDCS) electrodes according to embodiments of the present disclosure.

FIG. 3 depicts the placement of stimulating electrodes, fNIRS light sources and sensors, and EEG electrodes on a head of a subject. The electrodes are represented by small circles. E represents EEG electrodes, S represents light source electrodes, and D represents sensors. Stimulation sites are represented by bold dashed circles. Bold lines connecting electrodes or sensors represent data channels of interest. The present invention functions by placing the stimulating electrodes (represented by bold dashed circles) at locations that will focus the effects of the stimulation on the brain region desired (e.g., motor cortex and/or dlPFC) while still allowing very concentrated recordings of the spatial areas of the regions by the functional near infrared spectroscopy (fNIRS) sensors (i.e., "S" or "D").

Figure 4C:
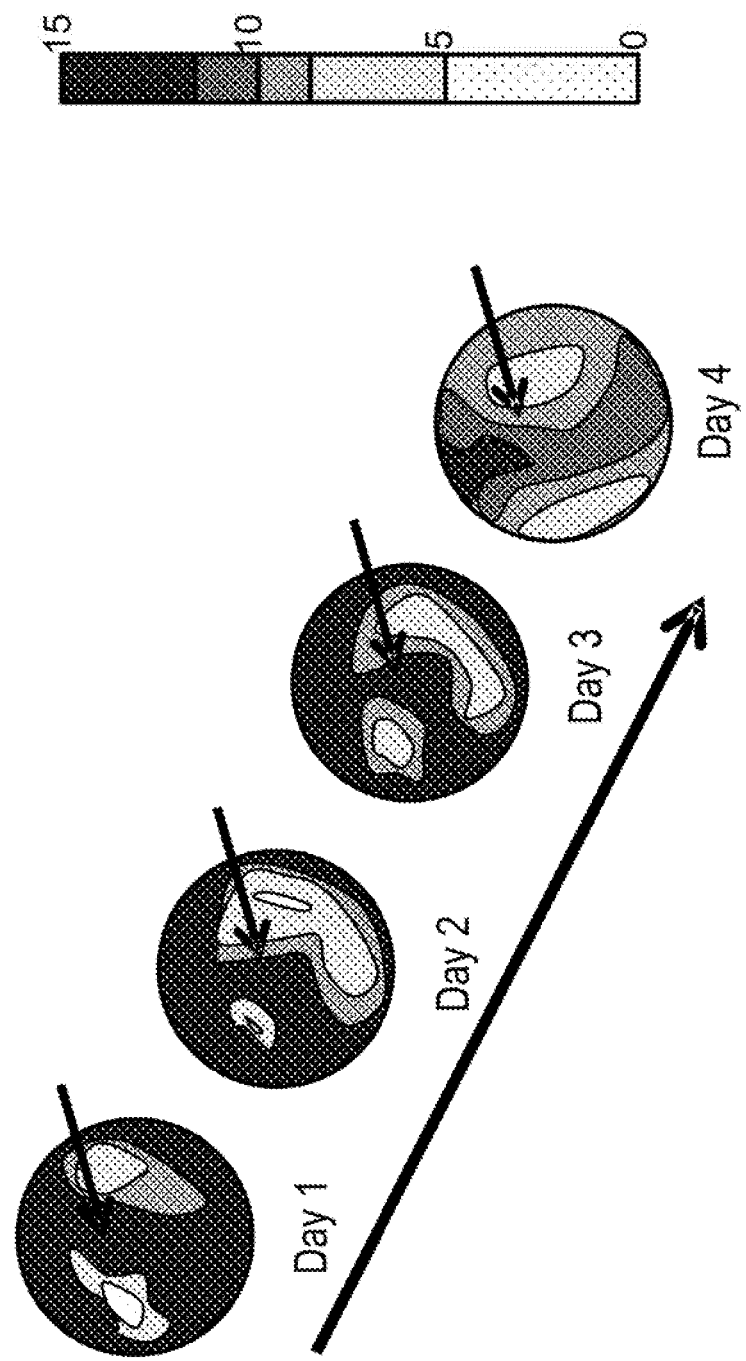
FIG. 4C is an illustration of topographic maps of wavelet-transformed data according to embodiments of the present disclosure.

Additionally, the EEG electrodes are not interfered with and provide detailed coverage over the entire head allowing for maximal information received. This information can then be analyzed and used to reset the stimulation parameters based on the accurate recordings made from the stimulation. FIGS. 4A, 4B and 4C show results of the montage depicted in FIG. 3, providing evidence of the ability of both EEG and fNIRS to record changes that occur during stimulation with this montage. A sham stimulation (FIG. 4A) (i.e., control condition) indicates a stimulation protocol that conveys the perception of being stimulated to the subject, but does not deliver the current to the brain. FIG. 4B depicts the actual stimulation condition in which the current is delivered to the dlPFC as depicted. Without a montage such as the one illustrated in FIG. 3, these changes would not be able to be analyzed and understood.

Specifically, FIGS. 4A and 4B depict simultaneous recording of fNIRS with tDCS showing the difference in location activities caused by tDCS. FIG. 4C depicts simultaneous recording of EEG with tDCS showing the difference in timing activities caused by tDCS. FIG. 4C illustrates topographic maps of wavelet-transformed data. The smaller arrows point to significant changes in the midline frontal theta spectral power across days, which corresponds to skill acquisition. The large arrow depicts the progression of the subjects over the training regime of 4 days.

Figure 5:
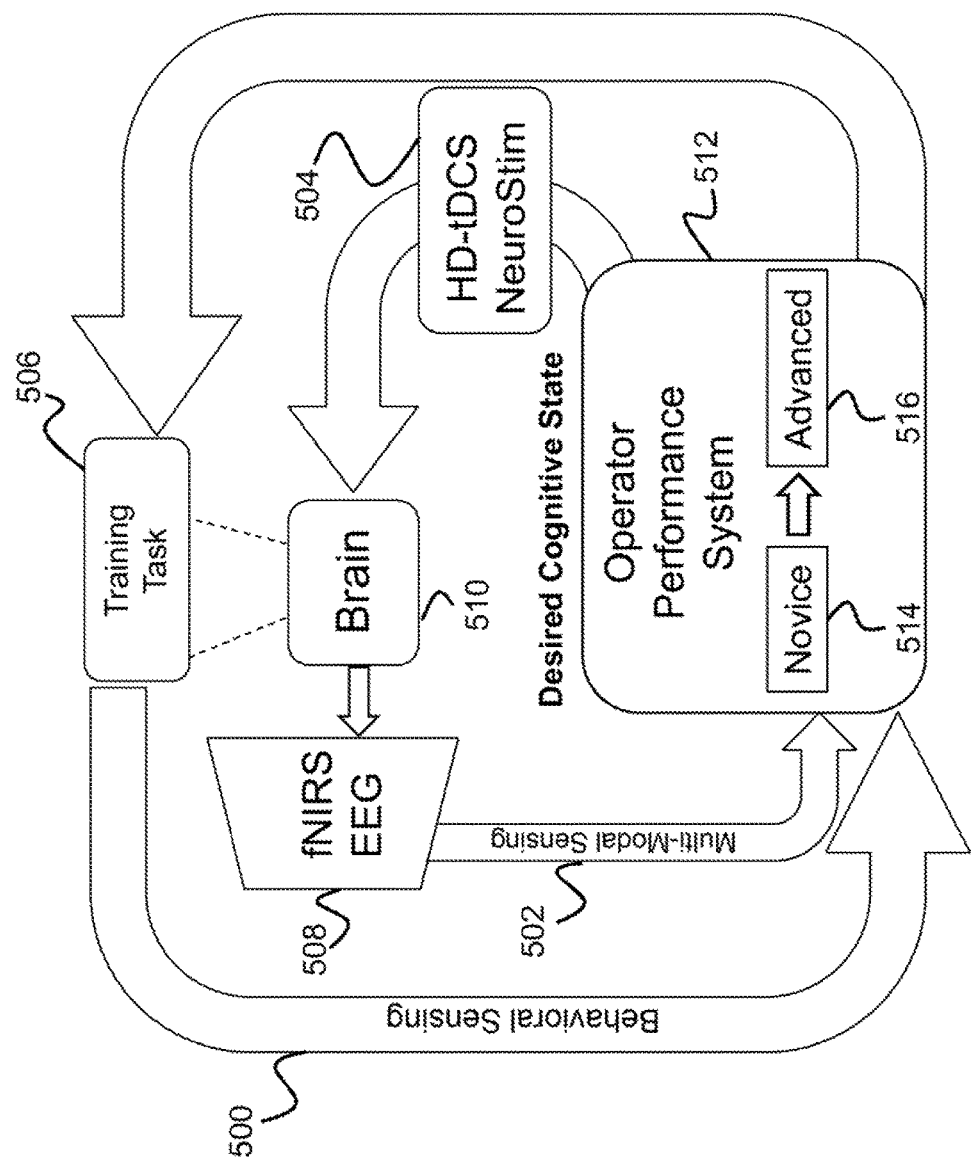
FIG. 5 is an illustration of a closed loop system for adjusting neurostimulation parameters according to various embodiments of the present disclosure.

Closed loop stimulation adaptation is unique to the present invention. FIG. 5 illustrates the architecture for a closed stimulation adaptation that measures behavioral output (e.g., piloting improvements) via behavioral sensing 500 and multi-modal sensing 502 to adapts the stimulation (HD-tDCS neurostimulation 504) to a pattern that is fitting for the current skill level of the user and a training task 506 at hand. Behavioral sensing is performed by, for example, custom software written to read flight-recorder-like data from the simulation, which was then used to compare the behavioral performance within subjects an also across subject conditions. Behavioral sensing are specific to the skill being trained. For example, the behavioral sensing may be based on quantitative metrics known to one skilled in the art, such as flight simulation data related to pilot skill, including measuring G-force at landing and other measures of aircraft flight operations. Multi-modal sensing 502 is performed by, for instance, fNIRS and EEG 508, which record neural activity in the brain 510 of the user. In combination with an operator performance system 512, the measurements from the multi-modal sensing 502 are used to automatically adjust stimulation parameters for HD-tDCS neurostimulation 504 of areas of the user's brain 510 in order to reach a desired cognitive state to improve the user's performance of the training task 506. The automatic adjustment includes an increase or decrease of neurostimulation at particular brain locations (e.g., motor cortex, dlPFC) is performed, as described below.

For example, the system according to various embodiments can be used to assist a complete novice being introduced to a task in which they must fly a plane through high turbulence. Using the present invention, the user will receive a computed stimulation (HD-tDCS neurostimulation 504) in a specific area, such as the motor cortex. The stimulation (HD-tDCS neurostimulation 504) is computed based on recordings from expert pilots and other novice pilots as well as a comparison of their fNIRS and EEG measurements and behaviors to the current novice pilot. It is critical to determine the typical variance of various novice pilots to optimize learning and stimulation parameters.

In addition, individual phenotypes of behavior can be used to personalize stimulation montage for optimum learning. However, as the current novice pilot's performance improves, the model adapts the stimulation to decrease stimulation in the motor cortex, but increase the decision making aspect of the pilot's brain and target the dlPFC. This adjustment is performed as an evolving system that adapts stimulation based on the current recorded expert pilots and the novice pilot's improvements. The goal is to improve the performance of the novice 514 pilot to the skill level of the advanced 516 pilot.

Figure 6:
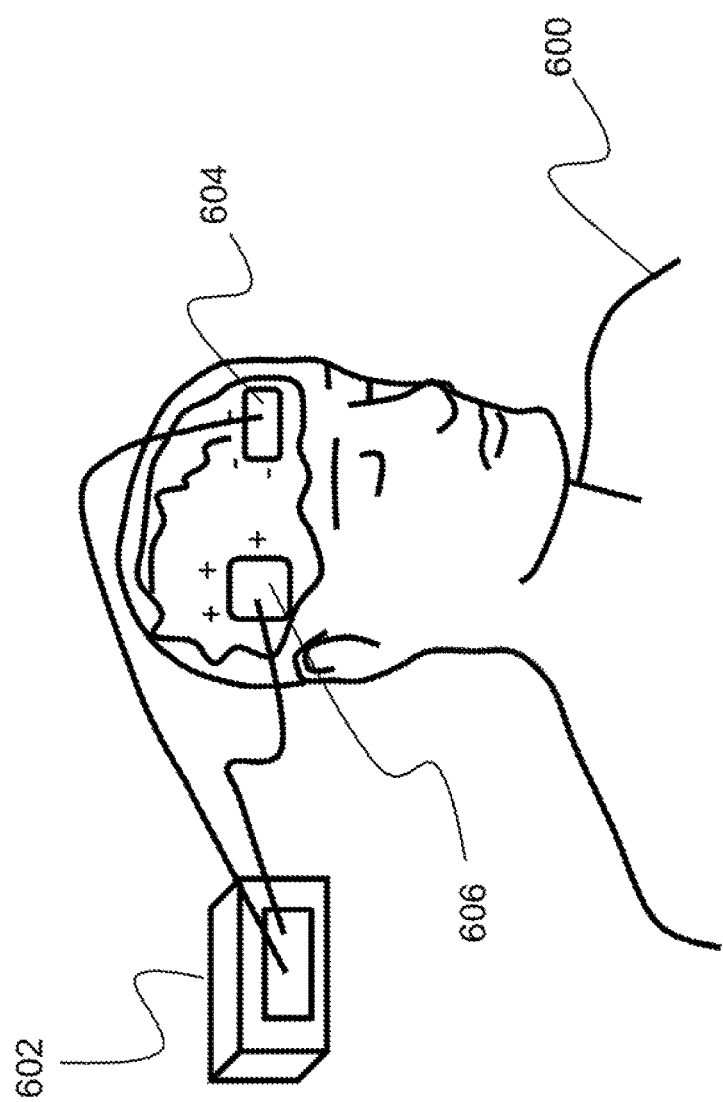
FIG. 6 illustrates a human subject receiving neurostimulation via a neural device according to some embodiments of the present disclosure.

FIG. 6 illustrates a human subject 600 receiving neurostimulation according to some embodiments of the present disclosure. A neural device 602 able to generate an electrical current delivers neurostimulation by applying a current through one electrode 604 (e.g., anode), and it flows through the brain to another electrode 606 (e.g., cathode). The neural device 602 is depicted as a patch that adheres to a portion of the patient's head. Any suitable neural device 602 can be used (such as the neural cap described below) provided that it can control stimulation of specific neural regions while performing recordings from the neural device 602 using a targeted arrangement of stimulating electrodes and recording electrodes and sensors of the neural device 602.

Figure 7:
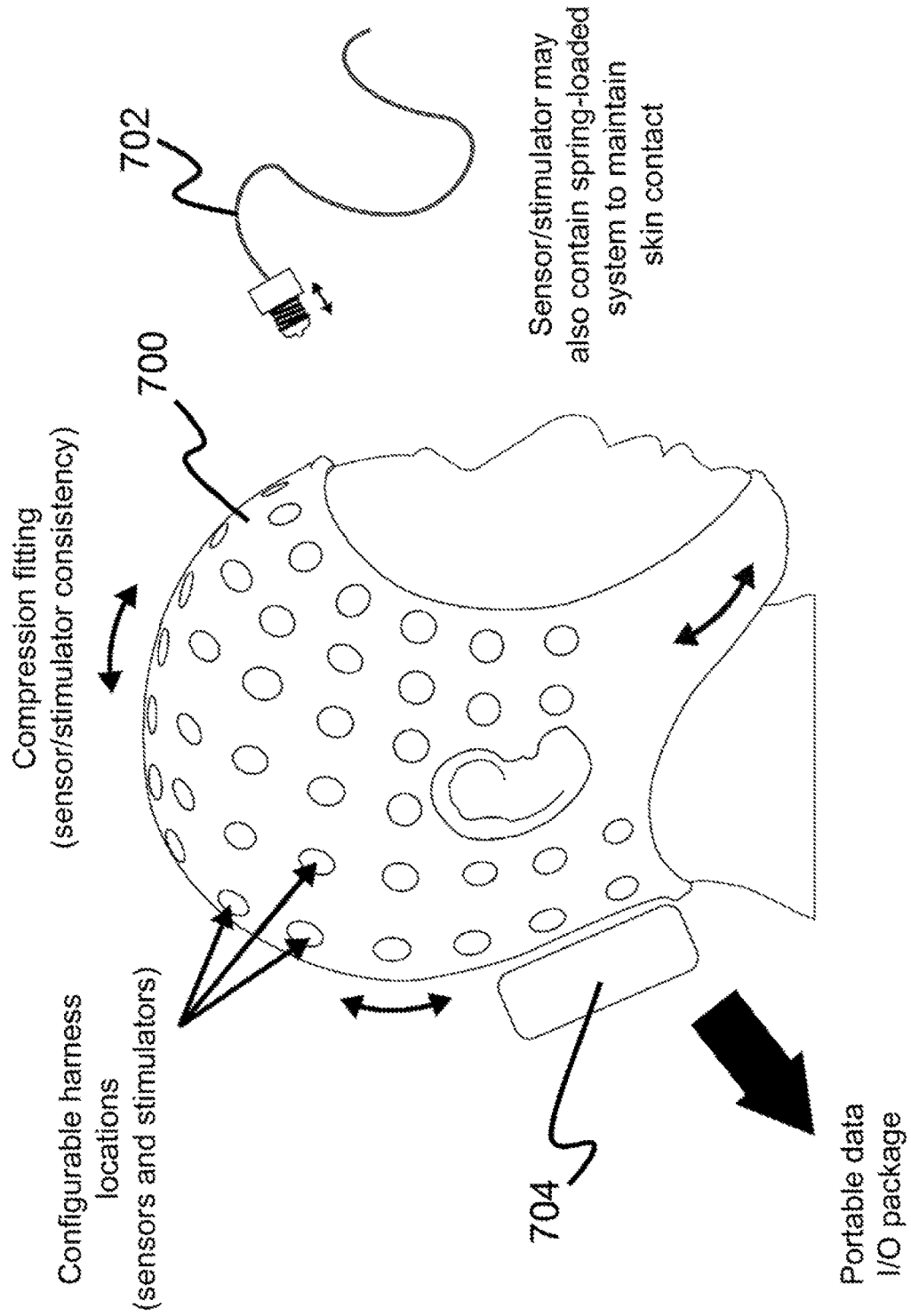
FIG. 7 illustrates a neural cap worn by a human subject for sensing and neurostimulation according to embodiments of the present disclosure.

FIG. 7 illustrates a neural device worn by a human subject for sensing and neurostimulation according to embodiments of the present disclosure. As depicted in FIG. 7, the neural device is a neural cap 700. As shown, the neural cap 700 may have configurable harness locations for stimulators and sensors. Additionally, the sensor/stimulator may contain a spring-loaded system 702 to maintain skin contact. Compression fitting of the neural cap 700 achieves sensor/stimulator consistency. Furthermore, the neural cap 700 can be connected to portable data input/output (I/O) package 704.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:
1. A system for automatic adjustment of neurostimulation, the system comprising:
   a neural device comprising a targeted arrangement of stimulating electrodes and recording electrodes and sensors configured to record neural data and apply neurostimulation; and one or more processors and a non-transitory memory having instructions encoded thereon such that when the instructions are executed, the one or more processors perform operations of:
  accessing a set of recorded behavioral data and recorded neural data comprising behavioral and neural recordings obtained from at least one expert in a skill and behavioral and neural recordings of at least one novice in a skill;
  determining stimulation parameters for a first neurostimulation based on a comparison of a first set of behavioral and neural recordings obtained from a current novice in the skill and the behavioral and neural recordings obtained from the at least one expert and the at least one novice in the skill;
  causing the first neurostimulation to be applied, via the neural device, to at least one of a motor cortex and a dorsal lateral prefrontal cortex of the current novice while simultaneously obtaining a second set of behavioral and neural recordings; and
  assessing skill improvement and any relative shift in locational brain activity between the first set of neural recordings and the second set of neural recordings;
  adjusting the stimulation parameters and causing a second neurostimulation to be applied, whereby the second neurostimulation increases or decreases stimulation in the motor cortex relative to the first neurostimulation and increases or decreases stimulation in the dorsal lateral prefrontal cortex relative to the first neurostimulation based on the assessed skill improvement.

2. The system as set forth in claim 1, wherein the second neurostimulation decreases stimulation relative to the first neurostimulation in the motor cortex and increases stimulation relative to the first neurostimulation in the dorsal lateral prefrontal cortex when the second set of behavioral and neural recordings indicate improvement in the skill.

3. The system as set forth in claim 1, wherein the neural device comprises electroencephalogram (EEG) electrodes and functional near-infrared spectroscopy (fNIRS) sensors.

4. The system as set forth in claim 3, wherein the neural device comprises transcranial direct current stimulation (tDCS) electrodes, and wherein the EEG electrodes are configured to record neural activity of the entire brain, the fNIRS sensors are configured to record neural activity of specific neural regions, and the tDCS electrodes are configured to apply stimulation to specific neural regions.

5. The system as set forth in claim 1, wherein the neural device is a neural cap.

6. A computer-implemented method for automatic adjustment of neurostimulation, comprising:
  an act of causing one or more processors to execute instructions stored on a non-transitory memory such that upon execution, the one or more processors perform operations of:
    accessing a set of recorded behavioral data and recorded neural data comprising behavioral and neural recordings obtained from at least one expert in a skill and behavioral and neural recordings of at least one novice in a skill;
    determining stimulation parameters for a first neurostimulation based on a comparison of a first set of behavioral and neural recordings obtained from a current novice in the skill and the behavioral and neural recordings obtained from the at least one expert and the at least one novice in the skill,
    wherein the neural recordings obtained from the current novice are recorded via a neural device comprising a targeted arrangement of stimulating electrodes and recording electrodes and sensors configured to record neural data and apply neurostimulation;
    causing the first neurostimulation to be applied, via the neural device, to at least one of a motor cortex and a dorsal lateral prefrontal cortex of the current novice while simultaneously obtaining a second set of behavioral and neural recordings; and
    assessing skill improvement and any relative shift in locational brain activity between the first set of neural recordings and the second set of neural recordings;
    adjusting the stimulation parameters and causing a second neurostimulation to be applied, whereby the second neurostimulation increases or decreases stimulation in the motor cortex relative to the first neurostimulation and increases or decreases stimulation in the dorsal lateral prefrontal cortex relative to the first neurostimulation based on the assessed skill improvement.

7. The method as set forth in claim 6, wherein the second neurostimulation decreases stimulation relative to the first neurostimulation in the motor cortex and increases stimulation relative to the first neurostimulation in the dorsal lateral prefrontal cortex when the second set of behavioral and neural recordings indicate improvement in the skill.

8. The method as set forth in claim 6, wherein the neural device comprises electroencephalogram (EEG) electrodes and functional near-infrared spectroscopy (fNIRS) sensors.

9. The method as set forth in claim 8, wherein the neural device comprises transcranial direct current stimulation (tDCS) electrodes, and wherein the one or more processors further perform operations of:
  causing the EEG electrodes to record neural activity of the entire brain;
  causing the fNIRS sensors to record neural activity of specific neural regions; and
  causing the tDCS electrodes to apply stimulation to specific neural regions.

10. A computer program product for automatic adjustment of neurostimulation, the computer program product comprising:
  computer-readable instructions stored on a non-transitory computer-readable medium that are executable by a computer having one or more processors for causing the processor to perform operations of:
    accessing a set of recorded behavioral data and recorded neural data comprising behavioral and neural recordings obtained from at least one expert in a skill and behavioral and neural recordings of at least one novice in a skill;
    determining stimulation parameters for a first neurostimulation based on a comparison of a first set of behavioral and neural recordings obtained from a current novice in the skill and the behavioral and neural recordings obtained from the at least one expert and the at least one novice in the skill,
    wherein the neural recordings obtained from the current novice are recorded via a neural device comprising a targeted arrangement of stimulating electrodes and recording electrodes and sensors configured to record neural data and apply neurostimulation;
    causing the first neurostimulation to be applied, via the neural device, to at least one of a motor cortex and a dorsal lateral prefrontal cortex of the current novice while simultaneously obtaining a second set of behavioral and neural recordings; and assessing skill improvement and any relative shift in locational brain activity between the first set of neural recordings and the second set of neural recordings;

adjusting the stimulation parameters and causing a second neurostimulation to be applied, whereby the second neurostimulation increases or decreases stimulation in the motor cortex relative to the first neurostimulation and increases or decreases stimulation in the dorsal lateral prefrontal cortex relative to the first neurostimulation based on the assessed skill improvement.

11. The computer program product as set forth in claim 10, wherein the second neurostimulation decreases stimulation relative to the first neurostimulation in the motor cortex and increases stimulation relative to the first neurostimulation in the dorsal lateral prefrontal cortex when the second set of behavioral and neural recordings indicate improvement in the skill.

12. The computer program product as set forth in claim 10, wherein the neural device comprises electroencephalogram (EEG) electrodes, functional near-infrared spectroscopy (fNIRS) sensors, and transcranial direct current stimulation (tDCS) electrodes, and wherein the computer program product further comprises instructions for causing the one or more processors to further perform operations of:

causing the EEG electrodes to record neural activity of the entire brain;

causing the fNIRS sensors to record neural activity of specific neural regions; and causing the tDCS electrodes to apply stimulation to specific neural regions.

\* \* \* \* \*